US006939562B2

(12) United States Patent
Spiro et al.

(10) Patent No.: US 6,939,562 B2
(45) Date of Patent: Sep. 6, 2005

(54) COLLAGEN/POLYSACCHARIDE BILAYER MATRIX

(75) Inventors: Robert C. Spiro, Half Moon Bay, CA (US); Lin Shu Liu, Sunnyvale, CA (US)

(73) Assignee: Depuy Acromed, Inc., Raynham, MA (US)

( * ) Notice: Subject to any disclaimer, the term of this patent is extended or adjusted under 35 U.S.C. 154(b) by 0 days.

(21) Appl. No.: 10/868,043

(22) Filed: Jun. 14, 2004

(65) Prior Publication Data

US 2004/0224027 A1 Nov. 11, 2004

Related U.S. Application Data

(62) Division of application No. 09/652,604, filed on Aug. 30, 2000, now Pat. No. 6,773,723.

(51) Int. Cl.[7] .................. A61K 31/715; A61K 38/16; A61K 9/70; C08H 1/02; B32B 5/32
(52) U.S. Cl. .................. 424/488; 424/78.3; 424/486; 428/316.6; 514/1; 514/2; 514/23; 530/402
(58) Field of Search ................. 424/486, 488, 424/78.3; 428/316.6; 514/1, 2, 23; 530/402

(56) References Cited

U.S. PATENT DOCUMENTS

| | | | |
|---|---|---|---|
| 4,784,989 A | 11/1988 | Hook et al. | |
| 4,837,285 A | 6/1989 | Berg et al. | |
| 4,841,962 A | 6/1989 | Berg et al. | |
| 4,902,289 A | 2/1990 | Yannas | |
| 5,157,111 A | 10/1992 | Pachence | |
| 5,273,900 A | 12/1993 | Boyce | |
| 5,489,304 A | 2/1996 | Orgill et al. | |
| 5,573,934 A | 11/1996 | Hubbell et al. | |
| 5,629,191 A | 5/1997 | Cahn | |
| 5,833,665 A | 11/1998 | Bootman et al. | |
| 5,837,226 A | 11/1998 | Jungherr et al. | |
| 5,866,165 A | 2/1999 | Liu et al. | |
| 5,906,997 A | 5/1999 | Schwartz et al. | |
| 5,916,585 A | 6/1999 | Cook et al. | |
| 5,972,385 A | 10/1999 | Liu et al. | |
| 5,997,895 A | 12/1999 | Narotam et al. | |
| 6,071,447 A | 6/2000 | Bootman et al. | |
| 6,080,194 A | 6/2000 | Pachence et al. | |

FOREIGN PATENT DOCUMENTS

WO  WO 97/06837  2/1997
WO  WO 99/13902  3/1999

OTHER PUBLICATIONS

Liu, L.–S., et al., "Local sustained release of growth factors from an implantable chondroitin sulfate scaffold for tissue regeneration ," Controlled Release Bioact. Mater., vol. 24, pp. 577–578, 1997.

Spiro, R.C., et al., "Inductive activity of recombinant human growth and differentiation factor–5," Biochemical Society Transactions, vol. 28, Part 4, pp. 362–368, 2000.

Block, J.E., et al., "Does xenogenic demineralized bone matrix have clinical utility as a bone graft substitute?," Medical Hypotheses, vol. 45, pp. 27–32, 1995.

Vonau, R.L., et al., "Combination of growth factors inhibits bone ingrowth in the bone harvest chamber," Clinical Orthopaedics and Related Research, No. 386, pp. 243–251, May 2001.

Liu, L.–S., et al., The bioactivity and stability of bFGF in a novel hyaluronate/heparin conjugate. Proceed. Int'l. Symp. Control. Release Bioact. Mater., vol. 26, pp. 1024–1025, Jul. 1999.

Liu, L.–S., et al., "An osteoconductive collagen/hyaluronate matrix for bone regeneration, "Biomaterials, vol. 20, pp. 1097–1108, 1999.

Radomsky, M.L., et al., "Novel formulation of fibroblast growth factor–2 in a hyaluronan gel accelerates fracture healing in nonhuman primates," Journal of Orthopaedic Research, vol. 17, No. 4, pp. 607–614, 1999.

Tay, B., et al., "Use of a collagen–hydroxyapatite matrix in spinal fusion, a rabbit model," Spine, vol. 23, No. 21, pp. 2276–2281, 1998.

Liu, L.–S. et al., "Hyaluronate derivatives–based matrices for growth factor delivery and tissue regeneration," Proc. Int'l. Symposium on Controlled Release of Bioactive Materials, vol. 25, pp. 996–997, Jun. 1998.

International Search Report, International Application No. PCT/US/96/13244 (WO 97/06837).

International Search Report, International Application No. PCT/US/98/18849 (WO 99/13902).

*Primary Examiner*—Robert A. Wax

(57) ABSTRACT

Disclosed are bilayer matrices of a polysaccharide such as collagen (COL) and another polysaccharide such as hyaluronic acid (HA) with various COL/HA ratios. Each layer has a porous structure. These materials are useful for tissue regeneration, particularly when used with orthopedic implants and drug delivery.

9 Claims, 1 Drawing Sheet

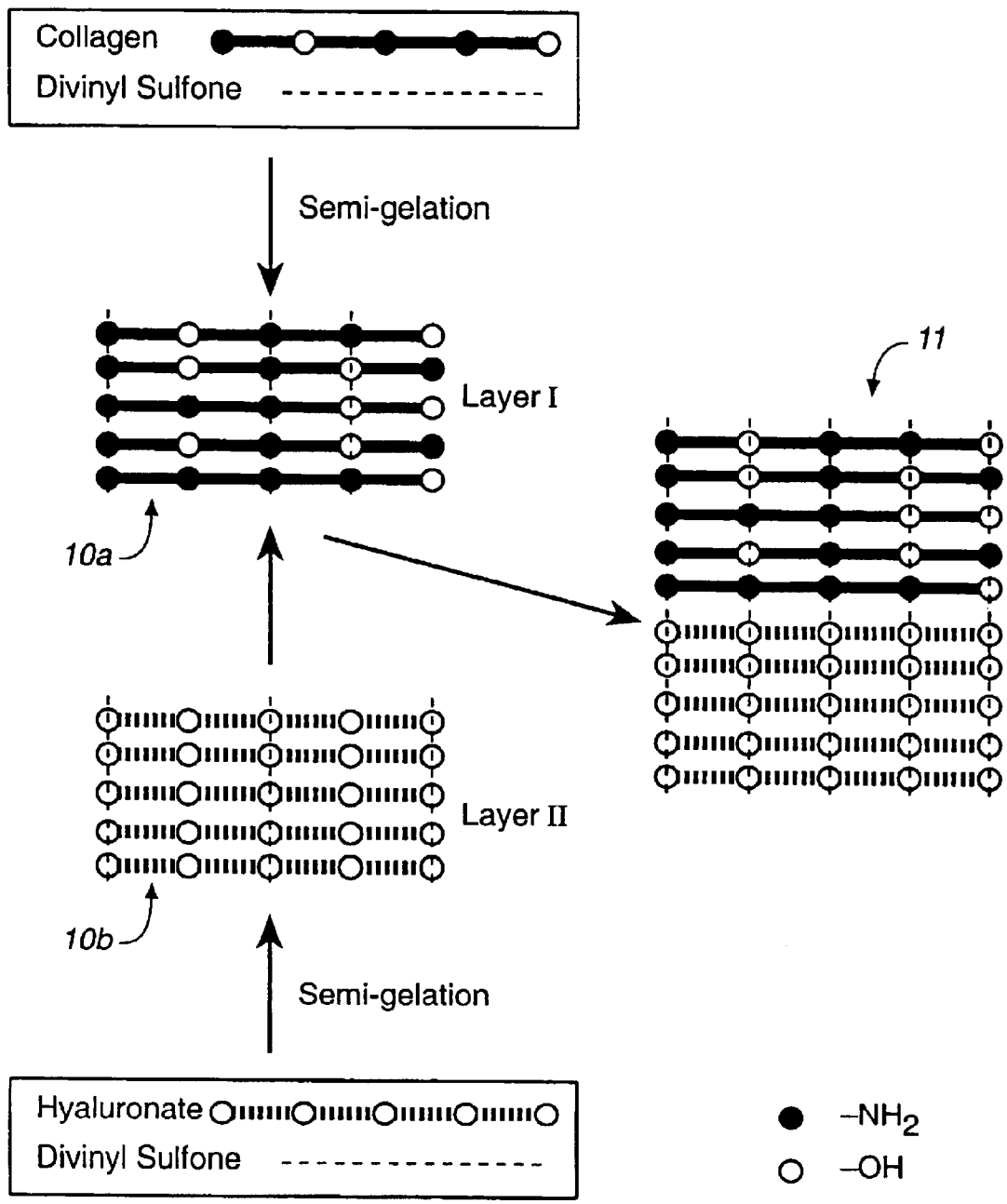
FIGURE

COLLAGEN/POLYSACCHARIDE BILAYER MATRIX

CROSS REFERENCE TO RELATED APPLICATIONS

This application is a divisional of prior application Ser. No. 09/652,604, entitled, "COLLAGEN/POLYSACCHARIDE BILAYER MATRIX" by Robert C. Spiro and Lin Shu Liu, filed on Aug. 30, 2000, now U.S. Pat. No. 6,773,723.

BACKGROUND OF THE INVENTION

The present invention is directed to biodegradable matrices for tissue regeneration.

Polysaccharides, such as glycosaminoglycans that include hyaluronic acid (HA) have been used in a wide variety of biomaterials. Hyaluronic acid (HA), a naturally-occurring polysaccharide, has been used in matrix engineering in ophthalmic and orthopedic medicine. Clinical indications for HA alone are limited by its physical properties and the short residence time of the natural HA molecule. A formaldehyde cross-linked HA, Hylan, has been used in viscosupplementation of arthritic diseased joints (Takigami et al., 1993, Carbohydrate Polymers 22: 153–160.

Berg et al., (U.S. Pat. No. 5,510,418, issued Apr. 4, 1996) disclose glycosaminoglycans, such as, HA, chondroitin sulfates, keratan sulfates, chitin and heparin, chemically conjugated to a synthetic hydrophilic polymer, such as polyethylene glycol (PEG) that are used as injectable formulations or solid implants. Kimata et al., (U.S. Pat. No. 5,464,942 issued Nov. 7, 1995) disclose phospholipid linked glycosaminoglycans and their use as metastasis inhibitors. Sakurai, et al, U.S. Pat. No. 5,310,881 issued May 10, 1994, disclose glycosaminoglycan-modified proteins. Balazs et al., U.S. Pat. No. 5,128,326 issued Jul. 7, 1992, disclose hyaluronan cross-linked with divinyl sulfone.

SUMMARY OF THE INVENTION

The present invention provides biodegradable matrices for tissue regeneration, methods of making the matrices and methods of using the matrices.

A biodegradable matrix of the present invention comprises two layers, each layer comprising a cross-linked polymeric component that differ in their composition, density, and porosity, wherein each of the polymeric components is a derivative of a member selected from the group consisting of collagen, albumin, fibrinogen, fibronectin, vitronectin, laminin, hyaluronic acid, dextran, dextran sulfate, chondroitin sulfate, dermatan sulfate, keratan sulfate, chitin, chitosan, heparin, heparin sulfate and alginate.

The two layers are attached by either mechanical adhesion or chemical cross-linking.

The biodegradable matrices are made by forming a layer by reacting a polymeric component with a cross-linking agent such as divinyl sulfone or a dialdehyde. Then the second layer, which may be a slurry, is applied and may either mechanically adhere and gel onto the first layer or be chemically linked to the first layer by cross-linking agents. The second layer also comprises a cross-linked polymeric component.

The present invention also provides a method of using the matrix to regenerate tissue by applying the matrix at a site of desired tissue regeneration.

BRIEF DESCRIPTION OF THE DRAWING

The FIGURE is a schematic flow chart of the synthesis of an embodiment of a bilayer matrix according to the invention.

DESCRIPTION OF THE PREFERRED EMBODIMENTS

The matrices comprise at least two porous polymeric layers that differ in their composition, density and porosity, so that they have different characteristics within the environment of growing tissue. The two polymeric layers are separately prepared, then assembled either by chemically cross-linking or mechanical embedding. The layers will differ in at least one property among composition, density, porosity, and the nature of the cross-linking bond, but one or two of these properties may be the same for both layers.

In the present invention each of the polymeric components is selected from the group consisting of collagen, albumin, fibrinogen, fibronectin, vitronectin, laminin, hyaluronic acid, dextran, dextran sulfate, chondroitin sulfate, dermatan sulfate, keratan sulfate, chitin, chitosan, heparin, heparin sulfate and alginate. In a preferred embodiment, the polymeric component is a protein selected from the group consisting of collagen, albumin, fibrinogen, fibronectin, vitronectin and laminin. In another preferred embodiment the polymeric component is a polysaccharide selected from the group consisting of hyaluronic acid, dextran, dextran sulfate, chondroitin sulfate, dermatan sulfate, keratan sulfate, heparin, heparin sulfate, chitosan, chitin and alginate. In a preferred embodiment, the polymeric components are selected from the group consisting of hyaluronic acid and collagen. As used herein, the term "polymeric component" includes the polysaccharides or proteins and their salts such as the sodium, potassium, magnesium, calcium, and the like, salts. Preferred forms of starting material of the polymeric components include those which have been approved for human use. The starting material for hyaluronate can be derived by bacterial fermentation or through isolation from rooster combs or can be obtained from commercial sources.

Each layer may be comprised of the same or different polymeric components. In one preferred embodiment, the polymeric component in both layers is collagen. In another preferred embodiment, one layer comprises HA and the other comprises collagen. Typically, the polysaccharides will have an average molecular weight of about 1,000 to 10,000,000 DA.

A matrix of the present invention may be formulated in several physical forms, including sponge-like forms.

Drugs, growth factors, polypeptides, proteins, cDNA, gene constructs and other bioactive therapeutic agents may also be included in the matrix and can be entrapped within the sponge either by mixing the agent with one of the two derivatives before gelatinization, or diffusion from a drug solution into the sponge after their formation.

The agent may also be covalently linked to the matrix.

The matrix may be formulated into a sponge-like material that is desirable for an implantable formulation. The matrices of the present invention may be formed into any shape by lyophilization or air drying in molds of the desired shape.

Growth factors and/or therapeutic agents may be included in the matrix, and can include proteins originating from various animals including humans, microorganisms and plants, as well as those produced by chemical synthesis and using genetic engineering techniques. Such agents include, but are not limited to, biologically active substances such as growth factors such as, bFGF, aFGF, EGF (epidermal growth factor), PDGF (platelet-derived growth factor), IGF (insulin-like growth factor), TGF-$\beta$ 1 through 3, including the TGF-$\beta$ superfamily (BMP=s, GDF-5, ADMP-1 and dpp); cytokines, such as various interferons, including interferon-alpha, -beta and -gamma, and interleukin-2 and -3; hormones, such as, insulin, growth hormone-releasing factor and calcitonin; non-peptide hormones; antibiotics; anti-cancer agents and chemical agents, such as, chemical mimetics of growth factors or growth factor receptors, and gene and DNA constructs, including cDNA constructs and genomic constructs. In a preferred embodiment, the agents include those factors, proteinaceous or otherwise, which are found to play a role in the induction or conduction of growth of bone, ligaments, cartilage or other tissues associated with bone or joints, such as for example, BMP and bFGF. The present invention also encompasses the use of autologous or allogeneic cells encapsulated within the matrix. The autologous cells may be those naturally occurring in the donor or cells that have been recombinantly modified to contain nucleic acid encoding desired protein products.

As will be understood by those of skill in the art, the amount of agent to be immobilized or encapsulated within the carrier will vary depending upon the intended target, but will usually be in the range of picogram to gram quantities.

A matrix of the present invention may be administered through implantation or direct application depending on the intended application.

Each of the two polymeric layers may be respectively synthesized by cross-linking, for example, collagen and hyaluronic acid (COL and HA). Typical cross-linking agents include divinyl sulfone (DVS) and polyaldehydes, such as, bi- or trialdehyde. If one of the layers comprises a polysaccharide, it can be prepared for cross-linking by opening sugar rings and reacting with sodium periodate to produce a polysaccharide derivative with free aldehyde end groups. For chemical assembling of two COL/HA polymeric layers with DVS, they should carry both active hydrogen atoms and sulfone functional groups attached on their surfaces. This may be attained by either controlling the ratio of COL/HA to the cross-linker or varying the gelation time.

Alternatively, the layers may be linked by thermal dehydration. For mechanical attachment of the layers, one layer should have pores large enough to allow the components of the second layer to penetrate where gelation can take place. Thus, control of both the viscosity and the ability to gel in solution of substances of the second layer are important. A slurry of the second layer material with low viscosity and long gelation time may penetrate to the entire first layer. These parameters are controlled so the slurry penetrates sufficiently into the first layer to form a strong mechanical bond, where it gels.

In one embodiment, the first polymeric layer is prepared by cross-linking a polysaccharide or protein to another polysaccharide or protein. The two polysaccharides or proteins may be the same or different from one another. For example, collagen may be cross-linked to collagen, or hyaluronate may be cross-linked to collagen. Various COL/HA ratios may be used. Typical ratios are 2:8 to 9:1 collagen to HA.

The first polymeric layer may then be applied, mechanically and/or chemically, to the second polymeric layer. Typical chemical application may be accomplished by cross-linking with DVS or a polyaldehyde linking agent.

The FIGURE schematically shows an embodiment of the process for forming the bilayer matrix. The collagen (COL) and hyaluronate (HA) are separately cross-linked with DVS to form respectively the cross-linked COL layer 10a and the cross-linked HA layer 10b. The layer 10a is cross-linked via hydroxy and amino groups on the peptide chains of collagen. The layer 10b is cross-linked via hydroxy groups of the polysaccharide. The layers 10a and 10b are then cross-linked to each other with DVS to form the bilayer product 11.

The biologically active substance may be incorporated during fabrication of the matrix between cross-linking or mechanical application of layers. Alternatively, the biological substance may be incorporated after the matrix is fabricated by soaking the matrix in a solution containing the active substance.

The efficacy of tissue regeneration can be shown by both in vitro and in vivo tests known by those of ordinary skill in the art. In the present invention, the preferred therapeutic agents are those factors which are found to play a role in the induction or conduction of growth of bone, ligaments, soft tissue, cartilage or other tissues associated with bone or joints. The matrix, which may include therapeutic agents as described above, will be applied at a site of desired tissue regeneration, such as bone growth, cartilage growth or joint repair.

In vitro and in vivo assays for the assessment of chondroinduction, chondroconduction, osteoinduction and osteoconduction are known by those of ordinary skill in the art. For the in vitro tests, primary fetal rat calvarial cells, harvested by a series of collagenase digestions, according to the method of Wong and Cohn (PNAS USA 72:3167–3171, 1975), or primary rat epiphyseal cartilage, according to the method of Thyberg and Moskalewski, (Cell Tissue Res. 204:77–94, 1979) or rabbit articular chondrocytes, harvested by the method of Blein-Sella O. et al., (Methods Mol. Biol., 43:169–175, 1995), are seeded into the carriers containing desired agents and cultured under conventional conditions for 1–4 weeks. Cultures are then processed and evaluated histologically.

The chondroconductive or chondroinductive capability of a matrix of the present invention can be determined by successful support of adhesion, migration, proliferation and differentiation of primary rat bone marrow and stromal cells as well as primary rat or rabbit chondrocytes. Bone marrow and bone marrow stromal cells are the source of chondroprogenitor cells found in the subchondral bone marrow of full-thickness defects. Bone marrow can be harvested from the long bones of 2–3 week-old inbred Lewis rats and can be added directly to a carrier or cultured for 2 weeks under standard conditions. The adherent stromal cell population that grows out of these cultures are passaged and frozen for use. Cells from up to six passages are used for culturing or seeding on the carrier to test for chondroconductive or chondroinductive capabilities.

Retinoic acid-treated chondrocytes represent a less mature chondrocyte and can be used to test the ability of matrices to support later stages of chondrogenesis. Retinoic acid treatment of primary chondrocytes is performed prior to culturing or seeding the cells on a carrier (Dietz, U. et al., 1993, J. Cell Biol. 52(1):57–68).

Cell adhesion and proliferation are monitored using an MTS assay that can measure cell number and viability based on mitochondrial activity. Stromal cells or chondrocytes are cultured on a carrier containing a therapeutic agent for 6–18 hrs. in the presence or absence of serum for adhesion analysis and for 1–2 weeks for proliferation assessment.

For cell migration testing, matrices are coated or fitted onto porous Trans-well membrane culture inserts (Corning). Stromal cells are seeded on top of the carrier in the upper chamber of the Trans-well and a chemoattractant (growth factor, PDGF) to placed in the bottom chamber. After 12–18 hrs of culture the cells that have migrated through the carrier to the bottom side of the Trans-well membrane are quantitated by the MTS assay. The matrix is removed from the upper chamber and processed histologically to assess the degree of infiltration.

The analysis of differentiation markers relevant to chondrogenesis and osteogenesis are evaluated at both the protein and transcriptional level. The specific markers that may be analyzed include: 1) Type II collagen and IIA, IIB isoforms; 2) Aggrecan proteoglycan; 3) Type IX, X and XI collagen; 4) Type I collagen; 5) Cartilage matrix protein (CMP); 6) Cart-1 transcription factor; 7) Fibronectin (EDA, EDB isoforms); 8) Decorin proteoglycan; 9) Link protein; 10) NG-2 proteoglycan; 11) Biglycan proteoglycan; 12) Alkaline phosphatase. Differentiation may be measured by Northern/PCR analysis, Western blotting or by metabolic cell labeling.

For Northern/PCR analysis, RNA is isolated by standard procedures from stromal cells or chondrocytes. Time course tests may be used to determine optimal culture periods that range from 1 to 6 weeks depending on the cell type. The isolated RNA is analyzed by Northern gel and hybridization techniques with specific cDNA or PCR amplified probes. Northern analysis is quantified by densitometric scanning of autoradiographs and normalization to housekeeping gene signals (G3PDH). Northern analysis may be supplemented with quantitative PCR analysis using primers generated from the published cDNA sequences of the genes to be analyzed.

For Western blotting, solubilized protein lysates are isolated from cells cultured on matrices containing osteogenic or chondrogenic agents by standard techniques (Spiro R. C., et al., 1991, J. Cell. Biol., 115:1463–1473). After the lysis of cells the matrix is extracted in stronger denaturants (8 M urea, GnHCL) to remove and examine bound or incorporated proteins. Protein samples are analyzed by standard Western blotting techniques using specific polyclonal or monoclonal antibodies.

For metabolic cell labeling, cells cultured on a matrix are metabolically radiolabeled with 35SO4, 35S-methionine or 3H/14C-labeled amino acids by standard techniques (Spiro et al., supra). Solubilized cellular and matrix-associated proteins are quantitatively immunoprecipitated with antibodies specific for the protein of interest and analyzed by SDS-PAGE (Spiro et al., supra). Quantitation of results are performed by densitometric scanning of autoradiographs and signals will be normalized to either cell equivalents or to a house-keeping protein such as actin.

Additionally, the ability of a matrix of the present invention to support chondrogeneic differentiation in vivo may be tested in an inbred rat soft tissue implant model. Rat bone marrow or stromal cells described above are seeded onto the carrier at high density, cultured overnight in MEM medium containing 10% FBS serum and antibiotics, then transferred into Millipore diffusion chambers and implanted intraperitoneally or subcutaneously into 8 week-old recipients. Chambers are harvested after 3 weeks and evaluated histologically for cartilage formation.

A transplantation model in outbred rats is used to evaluate the ability of the matrix to maintain the cartilage phenotype in vivo. Rib costal cartilage chondrocytes are seeded onto the carrier at high density and cultured overnight in Hams F-12 containing 1% rat serum and antibiotics. The seeded carriers are then implanted into posterior tibial muscle pouches created by blunt dissection in 8 week-old male Sprague-Dawley rats. Explants are taken at 14 and 28 days and evaluated histologically for compatibility, cartilage growth, and maintenance of the differentiated phenotype based on staining for aggrecan and type II collagen.

For the in vivo tests, a matrix may be evaluated for the capabilities for supporting osseous healing in a rat cranial defect model by implantation into a 5 mm by 3 mm defect created in the parietal bone of 6 weeks old male Sprague-Dawley rats. The defects are evaluated at 28 days by radiographic and histologic analysis.

The in vivo model for cartilage repair is a full-thickness articular cartilage defect in the rabbit (Amiel et al., 1985, J. Bone Joint Surg. 67A:911). Defects measuring approximately 3.7 mm in diameter and 5 mm deep defect are created in the center of the medial femoral condyles of adult male New Zealand white rabbits. The defects are then either filled with the matrix or left unfilled as controls. The defects are evaluated morphologically and histologically at 6 and 12 weeks and then at 6 months and one year.

The following examples are provided for purposes of illustration and are not intended to limit the invention in any way.

EXAMPLE 1

Preparation of a COL/HA bilayer matrix with 70% COL content in one layer and 100% HA content in another layer. This example illustrates how to cross-link a HA/DVS layer with a COL with HA gradient.

To 20 ml COL/HA suspension (560 mg of COL, Prep F fibers; 240 mg HA; 0.2N NaOH) added with 240 mg of DVS. The mixture was immediately blended using a heavy duty blender at low speed for 2×5 sec., and poured to a designed mold. After about 20 min. when the COL/HA slurry started to gel, 10 ml of HA/DVS viscose containing 400 mg HA and DVS was added onto the top of the COL/HA slurry. Since HA/DVS gels shortly after mixing, the viscose should be prepared only 4–5 min. before application by a vigorous vortexing. The mold with its content was allowed to sit on bench at room temperature for one hour to gel completely, then placed in 10% isopropyl alcohol solution for one hour. The matrix thus formed was washed with a large volume of D.I. water with several changes for 0.48 hours, followed by lyophilization.

EXAMPLE 2

Preparation of a COL/HA bilayer matrix with 100% COL content in one layer and 100% HA content in another layer. This example illustrates how to cross-link a HA/DVS layer to a COL/Glutaraldehyde layer.

COL matrix was prepared by cross-linking pre-fabricated COL sponge with glutaraldyhyde in 30% isopropyl alcohol by a regular procedure adopted in-house. The matrix was soaked in 0.2 N NaOH for 5 min. and placed in an appropriate mold. HA/DVS viscose was prepared as described in Example 1 and poured on the top of the COL matrix. After sitting on bench at room temperature for one hour, the matrix was immersed in 10% isopropyl alcohol for one hour, then large volumes of D.I. $H_2O$ with several changes for 48 hours, followed by lyophilization.

EXAMPLE 3

Preparation of a COL/HA bilayer matrix with 100% COL content in one layer and 100% HA content in another layer. This example illustrates how to cross-link a HA/DVS layer to a COL/DVS layer.

COL matrix was prepared by blending COL fiber (4%, 0.2 N NaOH) with DVS using a heavy duty blender at the low speed for 2×5 sec. The COL/DVS slurry thus formed was poured into an appropriate mold and allowed to sit on bench at room temperature for 30 min. HA/DVS viscose was prepared as described in Example 1 and poured on the top of the COL/DVS gel. After sitting on bench at room temperature for an additional hour, the matrix was lyophilized. The dried matrix was immersed in 10% isopropyl alcohol for one hour, then large volume of D.I. $H_2O$ with several changes for 48 hours, followed by lyophilization.

EXAMPLE 4

Preparation of a HA/DVS bilayer matrix with different cross-linking density in its two layers. This example illustrates the method to prepare HA/DVS bilayer get with a higher porosity in one layer and a lower one in the other through controlling their cross-linking degree.

400 mg HA in 10 ml 0.2 N NaOH was mixed with 400 µl DVS, mixed thoroughly, poured to a designed mold, then allowed to get at room temperature for 2 min. At this moment, 10 ml HA/DVS viscose (8% cross-linker and 4% HA) was poured onto the top of the HA gel previously molded. The bilayer gel continued to incubate at room temperature for another hour to allow the gelation to be completed. The gel was washed and lyophilized as described above.

EXAMPLE 5

Preparation of COL/HA bilayer matrix with different mass density in its two layers. This example illustrates the method to prepare HA/DVS bilayer gel with a higher porosity in one layer and a lower one in the other through controlling their mass density.

A COL/HA slurry [d, 70 mg/ml; 9:1 (COL/HA); 0.2 N NaOH] was mixed with DVS (75 mg/ml) by a vigorous blending, poured into a designed mold. Immediately, another part of COL/HA slurry with a lower mass density [d, 35 mg/ml; 9:1(CO/HA); 0.2 N NaOH] was mixed with DVS (35 mg/ml) and poured on the top of the first COL/HA gel. The matrix was then incubated at room temperature for another hour followed by lyphilization. The dried matrix was washed with a large volume of D.I. water and re-lyophilized.

EXAMPLE 6

Preparation of a COL/HA matrix with cross-linked HA in the core and 100% COL in the outside layer. This example illustrates how to embed a HA network into a COL gel using acid COL solution.

A HA/DVS matrix with the diameter of 8 mm, which was pre-swelled in PBS, was placed in the center of a well of 12 well tissue culture plate. 1.60 ml COL solution (Collagen Corporation, 3 mg/ml, 0.012 M HCl), 0.20 ml 10× PBS, and 0.20 ml 0.10 N NaOH were added into a 4 ml polypropylene round bottom tube, vortexed for 5 min., then incubated in a water bath at 37° C. The viscosity of the COL solution increased as time passed, and it finally became hard to flow along the wall when the tube was placed against both at a 60° angle from horizon. The viscose was carefully poured into the well and the plate was incubated at 37° C. for an additional 40 min., COL gel formed filling the space between the core HA matrix and the wall of the well. In this process, the penetration of COL viscose into the HA/DVS layer is dependent on its viscosity. Therefore, the COL viscose can be easily designed to only slightly penetrate into the core and gel only at the edge to create a firm physical cross-linking, while the integrity of two layers remains.

EXAMPLE 7

Preparation of COL/HA matrix with a COL gel in the core and HA/DVS in the outside layer. This example illustrates how to get a COL gel layer inside a HA/DVS matrix using acid COL solution.

A HA/DVS matrix disc in the size of 8×4 mm (r×d) was punched with a hole (r, 4 mm) in the center, swelled in PBS and placed in a tissue culture plate. A COL viscose prepared as described above was carefully poured into the hole. The plate continued incubating at 37° C. for an additional 40 min.

EXAMPLE 8

Identification of COL/HA bilayer matrices.

Synthetic COL/HA bilayer matrices were identified for their stability and structural appearance.

For the stability study, matrices thus prepared were immersed in PBS containing 1% penicillin/streptomycin and stored at 4° C. to prevent enzymatic degradation. After 2 months, no dissociation of two layers could be observed over all tested matrices, showing the stability of bilayer matrices thus formed.

Matrices prepared as illustrated above were stained with 0.01% toluidine blue, then with eosin. Two colors, blue and purple, were shown in the HA doman and COL domain respectively, indicating the formation of matrix with two separate layers.

EXAMPLE 9

Culture of COL/HA bilayer matrix seeded with FRC cell. This example illustrates the effect of the COL/HA ratio in two separate layers on cell attachment and differentiation.

Fetal rat calavarial (FRC) cells were seeded on a COL/HA bilayer matrix prepared as described in Example 6 at the density of $1.5 \times 10^6$ cell per ml HA/COL gel. 2.5 ml DMEM containing 2 µg GDF-5 was added to each well and cultured under traditional conditions.

After 24 hours, the medium was pipeted out, the matrix was washed with PBS, fixed with 10% formaline, stained with crystal violet, then examined by microscope observation. It was found that the cells attached in the COL domain were spread and those which attached in HA domain remained round.

EXAMPLE 10

Culture of COL/HA bilayer matrix pre-seeded with FRC cells. This illustrates the effect of differences in the composition of the two layers on-cell differentiation. Matrix prepared as described in example 3 was used. One bilayer matrix was soaked in a solution of FGF (+GF), and a second bilayer matrix was implanted without use of FGF (−GF). Matrix was cut to cubes of the size 8×6×4 mm (L, W, H), sterilized with ethanol, loaded with FRC cells at the density of $4 \times 10^5$ cell/specimen, and cultured at 37° C. in DMEM for 4 weeks. The medium was changed every other day. After 4 weeks, the matrix was removed from the medium, washed with PBS, and examined for cellular morphology by histology, counted for cell number by quantitation of DNA, measured for levels of alkaline phosphatase activity (ALP) by reacting with p-nitrophenol, and measured for sulfated glycosaminoglycans (GAGs) by the dimethylmethlene blue assay. Cells in the HA layer had a round, aggregated, and chondrocyte-like morphology, while those grown in the COL layer were flattened and spread. Biochemical analysis demonstrated that cells in the COL layer expressed a high level of ALP and a low level of GAGs compared to those in the HA layer (Table 1). These results demonstrate that the differentiation of cells within distinct regions of the bilayer matrix can be determined by specific compositional changes.

| Samples | Cell proliferation* | ALP** | Sulfate GAG |
|---|---|---|---|
| COL layer (+GF) | 6.88 | 61.8 | 0.45 ± 0.03 |
| COL layer (−GF) | 6.42 | 103 | −0.02 ± 0.06 |
| HA layer (+GF) | 5.53 | 7 | 2.53 ± 0.08 |
| HA layer (−GF) | 4.58 | 13 | 0.9 ± 0.1 |

*Cell proliferation, the rate of DNA amount in each specimen at day 28 to that at day 1.
**ALP, alkaline phosphatase activity, $\mu$mole/gDNA/min
***The O.D. at 595 nm of 5 times diluted de-stained solution

What is claimed is:

1. A multilayer biodegradable matrix for tissue regeneration, said matrix comprising two mechanically adhering layers, each of said layers comprising a cross-linked polymeric component selected from the group consisting of proteins, covalently cross-linked polysaccharides, and proteins covalently cross-linked to polysaccharides wherein each of said layers has a porosity sufficient to accommodate living cells therein.

2. A matrix according to claim 1 wherein said polymeric component is selected from the group consisting of collagen, albumin, fibrinogen, fibronectin, vitronectin, laminin, hyaluronic acid, dextran, dextran sulfate, chondroitin sulfate, dermatan sulfate, keratan sulfate, chitin, chitosan, heparin, heparin sulfate and alginate.

3. A matrix according to claim 1 wherein said proteins are selected from the group consisting of collagen, albumin, fibrinogen, fibronectin, vitronectin, and laminin.

4. A matrix according to claim 1 wherein said layers are different in chemical composition from each other.

5. A matrix according to claim 1 wherein said layers are different in physical density from each other.

6. A matrix according to claim 1 wherein said layers are different in structural porosity from each other.

7. A matrix of claim 4 wherein one layer comprises hyaluronate and another layer comprises collagen.

8. A matrix of claim 5 wherein one layer comprises hyaluronate and another layer comprises collagen.

9. A matrix of claim 6 wherein one layer comprises hyaluronate and another layer comprises collagen.

* * * * *